(12) United States Patent
Cusworth

(10) Patent No.: US 8,926,565 B2
(45) Date of Patent: Jan. 6, 2015

(54) INTRAVENOUS CATHETER SECUREMENT DEVICE

(76) Inventor: Loris Barbara Cusworth, Mitcham (AU)

(*) Notice: Subject to any disclaimer, the term of this patent is extended or adjusted under 35 U.S.C. 154(b) by 515 days.

(21) Appl. No.: 13/277,822

(22) Filed: Oct. 20, 2011

(65) Prior Publication Data
US 2013/0102968 A1 Apr. 25, 2013

(51) Int. Cl.
*A61M 5/32* (2006.01)
*A61M 25/02* (2006.01)

(52) U.S. Cl.
CPC ........ *A61M 25/02* (2013.01); *A61M 2025/0246* (2013.01); *A61M 2025/0273* (2013.01)
USPC .......................................... 604/179; 604/174

(58) Field of Classification Search
CPC ............. A61M 2025/0246; A61M 2025/0273; A61M 25/02
USPC .......................................... 604/174, 179, 180
See application file for complete search history.

(56) References Cited

U.S. PATENT DOCUMENTS

| 4,445,894 A | 5/1984 | Kovacs |
| 4,671,787 A | 6/1987 | Widman |
| 5,084,026 A | 1/1992 | Shapiro |
| 5,577,516 A | 11/1996 | Schaeffer |

*Primary Examiner* — Bhisma Mehta
*Assistant Examiner* — Bradley G Thomas, Jr.
(74) *Attorney, Agent, or Firm* — Crossley Patent Law

(57) ABSTRACT

An intravenous catheter securement device to secure an IV cannula, IV tubing, and attachments in place and to reduce the need for adhesive tape application, including a protective dressing body that secures an intravenous catheter between a cover flap and a lower portion thereof; a continuous pocket disposed between cover flap and the lower portion inner sides for securing a splint for immobilizing an IV site with minimal interference of the dressing body; an opening centrally disposed on the lower portion that serves as a viewing port over an IV site; a vertical slit centrally disposed on the lower portion between the front side and the opening that permits the dressing body to pass either side of a cannula and IV tube; and various attachment strips and tabs that secure an IV line to prevent kinking thereof and to prevent the IV line from weighing down on the cannula.

11 Claims, 3 Drawing Sheets

INTRAVENOUS CATHETER SECUREMENT DEVICE

BACKGROUND OF THE INVENTION

Various types of catheter wraps and supports are known in the prior art. However, what is needed is an intravenous catheter securement device that provides a comfortable, non-bruising, and non-irritating anchoring of an IV catheter into a patient's arm, that includes an opening for viewing a cannula, that allows the tubing that extends from the catheter to be disposed on top of the bandage, that reduces the potential for damage to the vein, that prevents leaking of the IV fluid into the surrounding tissues thereby causing swelling and pain. The present device solves the foregoing problems.

FIELD OF THE INVENTION

The present invention relates to intravenous catheters, and more particularly, to an intravenous catheter securement device.

SUMMARY OF THE INVENTION

The general purpose of the present intravenous catheter securement device, described subsequently in greater detail, is to provide an intravenous catheter securement device which has many novel features that result in an intravenous catheter securement device which is not anticipated, rendered obvious, suggested, or even implied by prior art, either alone or in combination thereof.

To accomplish this, the present intravenous catheter securement device includes a protective dressing body formed of a cover flap and a lower portion that secures an intravenous catheter when in use. Inner sides of each of the cover flap and the lower portion are continuously conjoined proximal to a rear side thereof along a rear seam disposed between the first and second sides. A first attachment strip is continuously disposed on the cover flap inner side proximal to the front side. A plurality of second attachment strips is continuously disposed on the cover flap exterior side proximal to the rear side between the first and second sides. A pocket is continuously disposed between the inner sides of the cover flap and the lower portion between the rear seam and the rear side and between the first and second sides. The pocket is provided to permit the insertion or removal of a splint for immobilizing an IV site without the need to interfere with other elements of the dressing body. An opening, which is centrally disposed on the lower portion between the front side and the rear side and between the first and second sides, is positioned directly over an IV site to serve as a viewing port. A vertical slit is centrally continuously disposed on the lower portion between the front side and the opening thus permitting the dressing body to pass either side of a cannula and an IV tube. The cover flap folds over the opening and is secured into place by a plurality of spaced-apart tabs. The cover flap further secures an IV site. Spaced-apart tabs are disposed on the lower portion inner side proximal to the opening. A third attachment strip is continuously disposed on the lower portion inner side between the first side and the second side in a central position between the front side and the first tab. The first and third attachment strips removably engage each other. A fourth attachment strip is continuously disposed on the lower portion exterior side proximal to the front side. The second and fourth attachment strips removably engage each other. The first, second, third and fourth attachment strips can be formed of hook and loop fastener. The attachment strips and the tabs secure an IV line to prevent kinking in the IV line and also to prevent the IV line from weighing down on the IV cannula. A clear sterile adhesive dressing is removably disposed within the opening to secure a cannula within a patient's vein.

The inner side of each of the cover flap and the lower portion is a soft material. The soft material can be a soft polar fleece. The soft material is designed to maintain warmth against a user's skin. The middle layer of each of the cover flap and the lower portion is a thin foam rubber material to provide cushioning for a comfortable yet secure IV site. The outer side of each of the cover flap and the lower portion is a water-resistant material. A logo is disposed on the cover flap exterior side for identification of the hospital or of another provider of services and goods in connection with the device.

The present intravenous catheter securement device is provided to hold an IV cannula, IV tubing, and attachments securely in place and to preserve the integrity of the skin by reducing the need for applying adhesive tape. The instance device also provides optimum patient comfort by cushioning between the attachments and the skin and further provides easy visual access to an IV site for nurse checks, without the need to remove and reapply bandages over the IV site. The device provides a simple and quick way to apply a splint, such as a light-weight aluminum splint, to immobilize a joint as necessary and to reduce the need for recannulation of patients while also reducing the time required to check and maintain IV sites by inserting the splint into the pocket. The device further provides a warm, comfortable, protected, and secure IV site. The water resistant outer layer protects an IV site against contamination and minor spillages. In addition, the present device provides a secure covering of an IV site to reduce the chance of interference from the patient and external influences as well.

The present device is strong, durable, water resistant, breathable, and warm while also being soft. The present device is also non-allergenic, washable, light-weight, flexible in conjunction with having the property of being capable of sterilization. The present device can be modified to suit other sites for cannulation, such as the wrist, the back of a hand or foot and to accommodate a wide range of sizes and ages of users. The device is also provided in a wide range of colors and motifs.

Thus has been broadly outlined the more important features of the present intravenous catheter securement device so that the detailed description thereof that follows may be better understood and in order that the present contribution to the art may be better appreciated.

BRIEF DESCRIPTION OF THE DRAWINGS

Figures

DETAILED DESCRIPTION OF THE DRAWINGS

Figure 1:
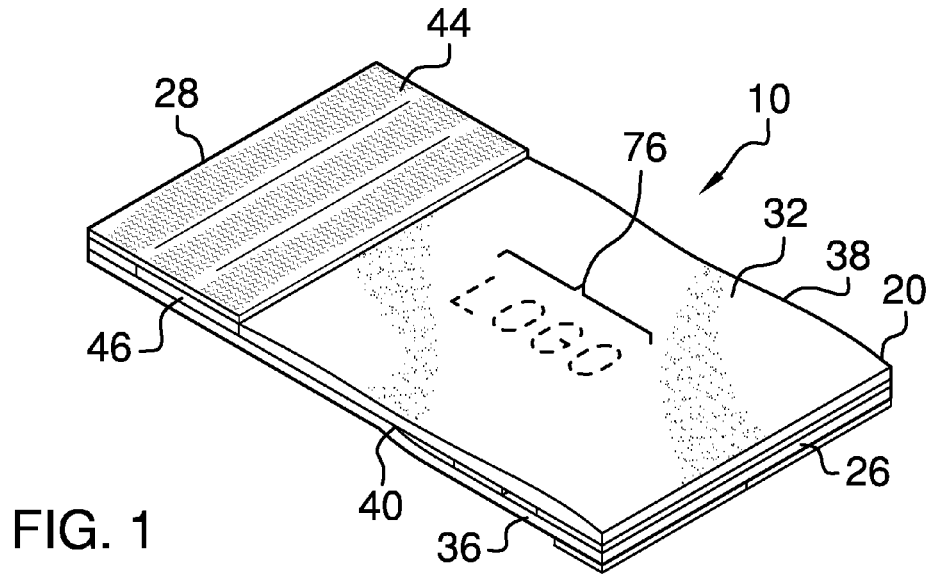
FIG. 1 is an isometric top view.
Figure 2:
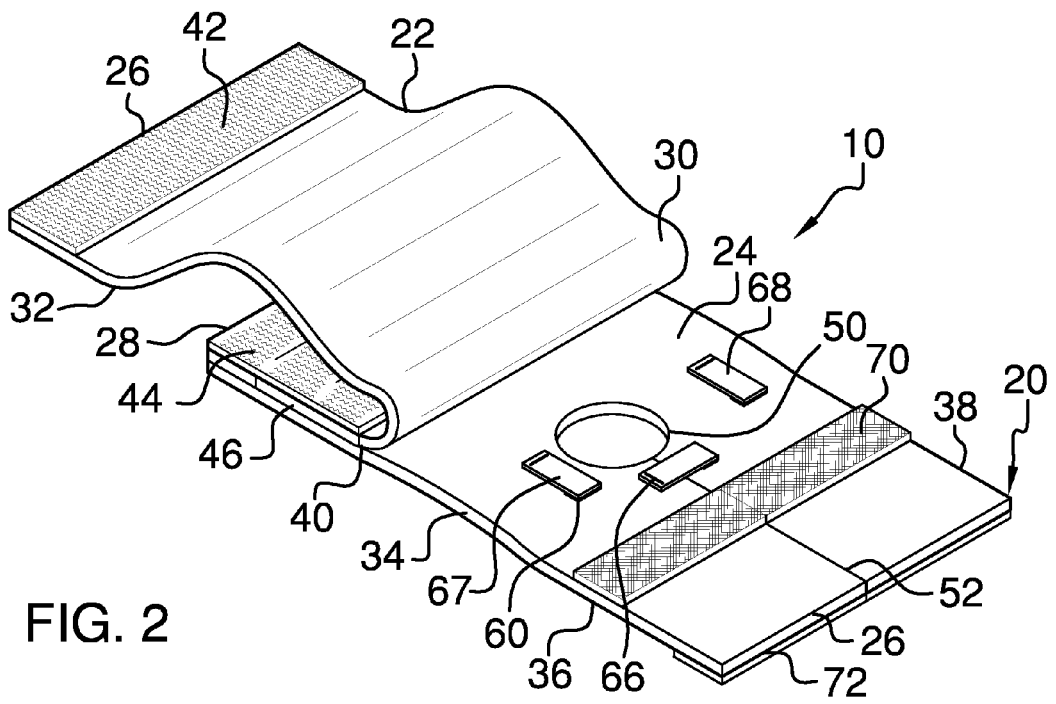
FIG. 2 is an isometric view in an open position.
Figure 3:
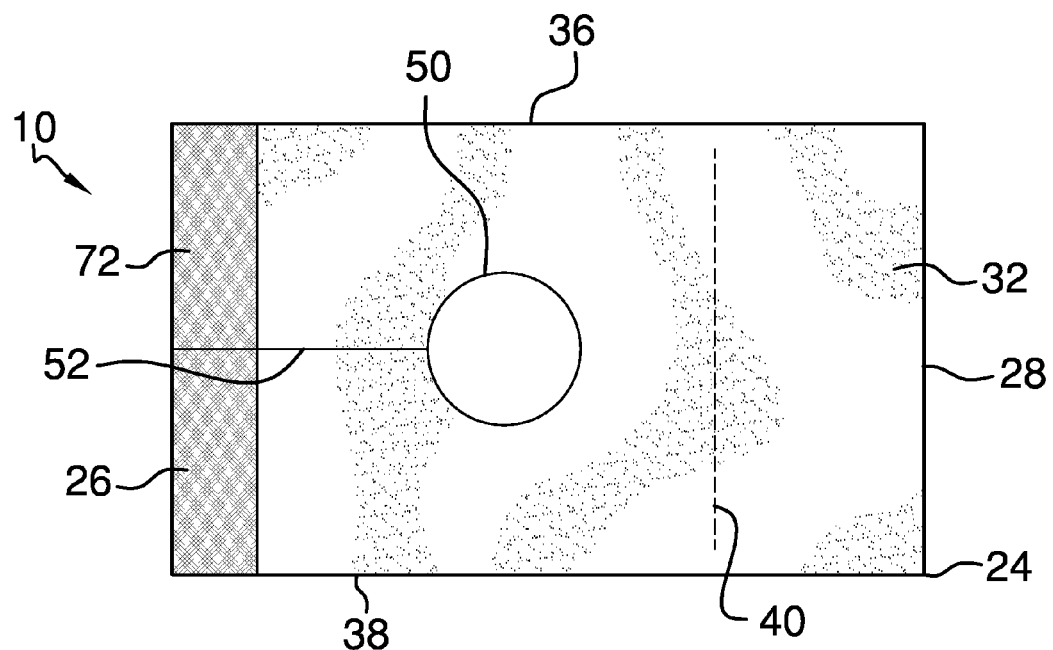
FIG. 3 is a rear elevation view.

With reference now to the drawings, and in particular FIGS. 1 through 6 thereof, example of the instant intravenous catheter securement device employing the principles and concepts of the present intravenous catheter securement device and generally designated by the reference number 10 will be described.

Referring to FIGS. 1 through 6 a preferred embodiment of the present intravenous catheter securement device 10 is illustrated. The intravenous catheter securement device 10 includes a protective dressing body 20 configured to secure an intravenous catheter 80 when in use. The dressing body 20 has a cover flap 22 and a lower portion 24. Each of the cover flap 22 and the lower portion 24 has a front side 26, a rear side 28, an inner side 30, an exterior side 32, a middle layer 34 continuously disposed between the inner side 30 and the exterior side 32, a first side 36, and a second side 38. The inner side 30 of each of the cover flap 22 and the lower portion 24 are continuously conjoined proximal to the rear side 28 along a rear seam 40 disposed between the first and second sides 36, 38.

A first attachment strip 42 is continuously disposed on the cover flap 22 inner side 30 proximal to the front side 26. A plurality of second attachment strips 44 is continuously disposed on the cover flap 22 exterior side 32 proximal to the rear side 28 between the first and second sides 36, 38. A pocket 46 is continuously disposed between the inner sides 30 of the cover flap 22 and the lower portion 24 between the rear seam 40 and the rear side 28 and between the first and second sides 36, 38. The pocket 46 is provided to permit the insertion or removal of a splint (not shown) for immobilizing an IV site without the need to interfere with other elements of the dressing body 20.

An opening 50 is centrally disposed on the lower portion 24 between the front side 26 and the rear side 28 and between the first and second sides 36, 38. A vertical slit 52 is centrally continuously disposed on the lower portion 24 between the front side 26 and the opening 50. The opening 50 is positioned directly over an IV site to serve as a viewing port. The slit 52 permits the dressing body 20 to pass either side of a cannula 82 and an IV tube 84.

A plurality of spaced-apart tabs 60 is disposed on the lower portion 24 inner side 30 proximal to the opening 50. Each of the tabs 60 comprises lower securement portion 61 and an upper securement portion 62 having a securement strip 63 disposed proximal to an internal outer edge 64 thereof removably attached to the lower securement portion 61. The tabs 60 comprise a first tab 66, a second tab 67, and a third tab 68. The first tab 66 is horizontally centrally disposed on the lower portion 24 inner side 30 with the lower securement portion 61 disposed on an opposite of the slit 52 from the upper securement portion 62. The second securement tab 67 is vertically disposed between the opening 50 and the first side 36 in a position closer to the opening 50 than the first side 36. The third securement tab 68 is vertically centrally disposed between the opening 50 and the second side 38.

A third attachment strip 70 is continuously disposed on the lower portion 24 inner side 30 between the first side 36 and the second side 38 in a central position between the front side 26 and the first tab 66. The first and third attachment strips 42, 70 removably engage each other.

A fourth attachment strip 72 is continuously disposed on the lower portion 24 exterior side 32 proximal to the front side 26. The second and fourth attachment strips 44, 72 removably engage each other. The first, second, third and fourth attachment strips 42, 44, 70, 72 can be formed of hook and loop fastener. The tabs 60 and the attachment strips 42, 44, 70, 72 secure an IV tube 84 to prevent kinking in the IV tube 84 and also to prevent the IV tube 84 from weighing down on the IV cannula 82. A clear sterile adhesive dressing (not shown) is removably disposed within the opening 50 to secure the cannula 82 within a patient's vein.

The inner side 30 of each of the cover flap 22 and the lower portion 24 is a soft material. The soft material can be a soft polar fleece. The middle layer 34 of each of the cover flap 22 and the lower portion 24 is a thin foam rubber material. The outer side 32 of each of the cover flap 22 and the lower portion 24 is a water-resistant material. The water resistant outer layer protects an IV site 85 against contamination and minor spillages. A logo 76 is disposed on the cover flap 22 exterior side 32.

Figure 4:
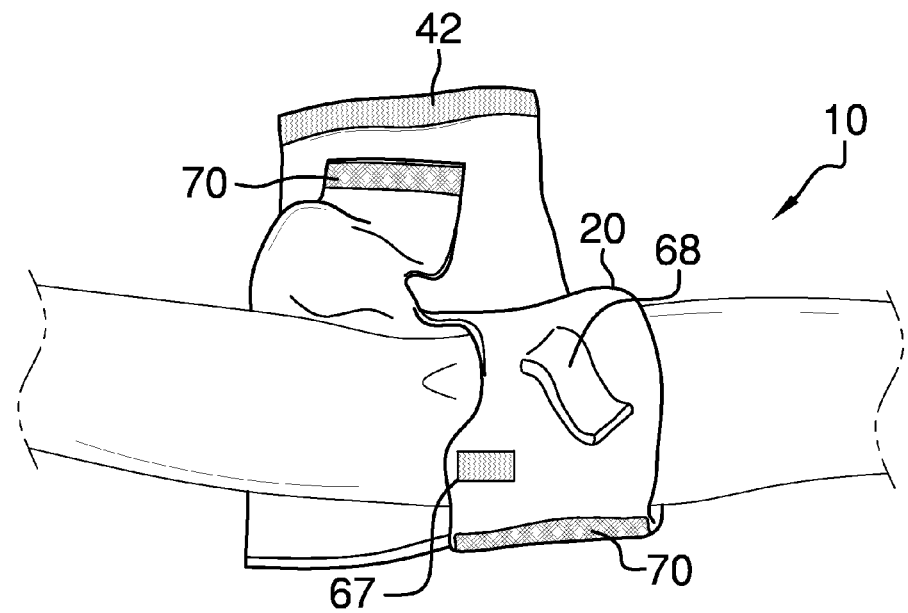
FIG. 4 is an in-use view partially wrapped around a patient's arm.
Figure 5:
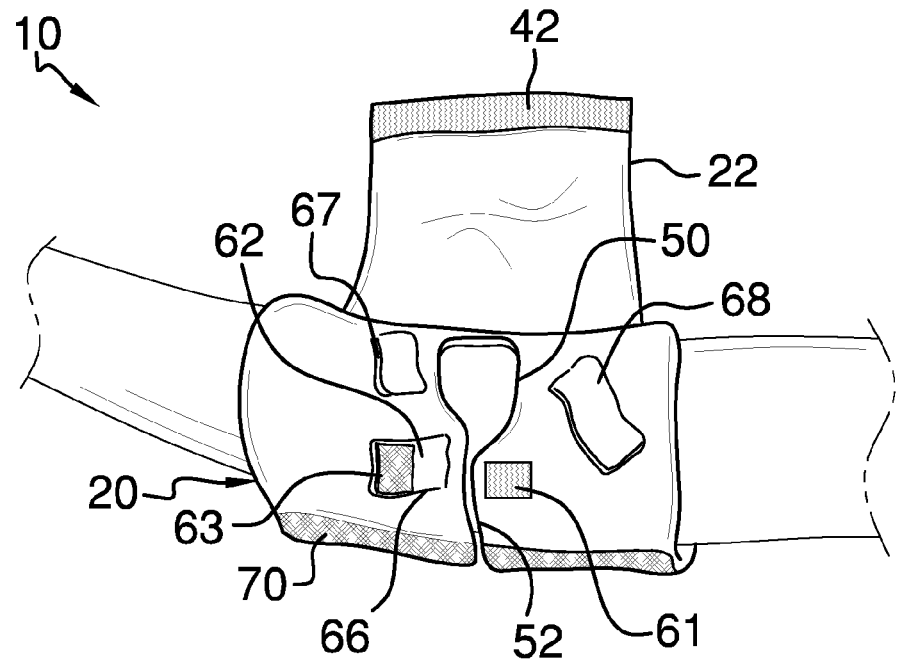
FIG. 5 is an in-use view secured around the patient's arm.
Figure 6:
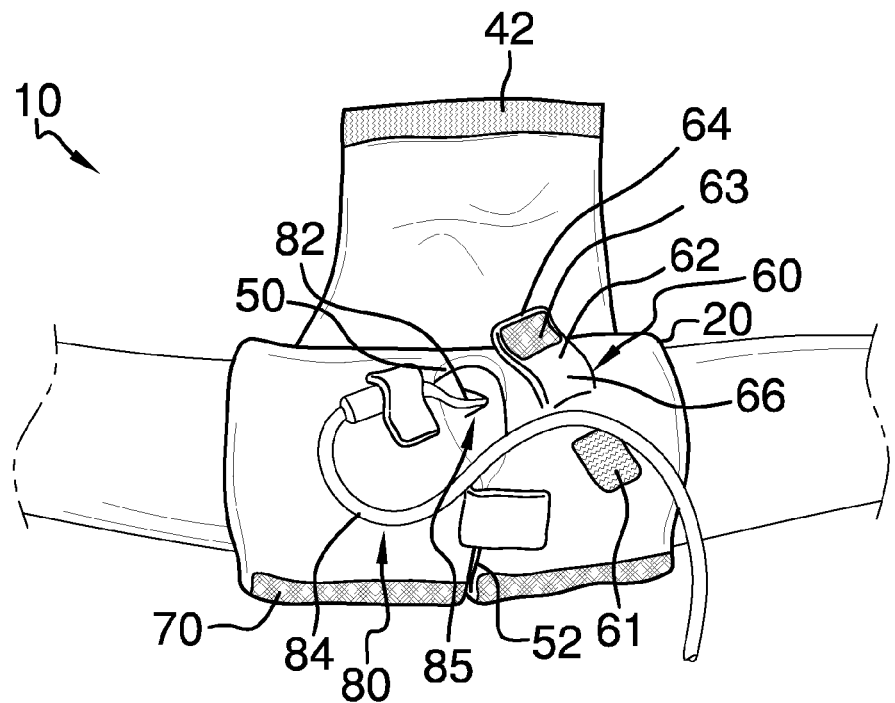
FIG. 6 is an in-use view with an IV catheter secured into place in the patient's arm.

Use:

To use the present device 10, the cannula 82 is inserted into a patient's vein in an IV site 85 and an IV tube 84 is attached to the cannula 82. The IV tube 84 is secured with steri-strips (not shown) and clear tape (not shown). Next, the dressing body 20 is wrapped around a patient's arm as illustrated in FIGS. 4 through 6 and the dressing body 20 is placed over the IV site 85 with the slit 52 disposed on each side of the cannula 82 so that the cannula 82 is visible through the opening 50 and the IV tube 84 is disposed atop the inner side 30 of the dressing body 20 lower portion 24. The IV tube 84 is secured into place atop the inner side 30 of the lower portion 24 using the tabs 60. The cover flap 20 first attachment strip 42 is attached to the lower portion 22 third attachment strip 70. Then the second and fourth attachment strips 44, 72 are removably engaged. If splinting is required, the patient's arm is straightened out and a user slides the splint into the pocket 46.

What is claimed is:

1. An intravenous catheter securement device comprising:
   a protective dressing body configured to secure an intravenous catheter when in use, the dressing body comprising:
   a cover flap;
   a lower portion, each of the cover flap and the lower portion has a front side, a rear side, an inner side, an exterior side, a middle layer continuously disposed between the inner side and the exterior side, a first side, and a second side;
   wherein the inner side of each of the cover flap and the lower portion are continuously conjoined proximal to the rear side along a rear seam disposed between the first and second sides;
   a first attachment strip continuously disposed on the cover flap inner side proximal to the front side;
   a plurality of second attachment strips is continuously disposed on the cover flap exterior side proximal to the rear side between the first and second sides;
   an opening centrally disposed on the lower portion between the front side and the rear side and between the first and second sides;
   a vertical slit is centrally continuously disposed on the lower portion between the front side and the opening;
   a plurality of spaced-apart tabs on the lower portion inner side proximal to the opening, each of the tabs comprising lower securement portion and an upper securement portion having a securement strip disposed proximal to an internal outer edge thereof removably attached to the lower securement portion;
   a third attachment strip is continuously disposed on the lower portion inner side between the first side and the second side in a central position between the front side and the first tab, wherein the first and third attachment strips removably engage each other;
   a fourth attachment strip is continuously disposed on the lower portion exterior side proximal to the front side, wherein the second and fourth attachment strips removably engage each other; and a pocket continuously disposed between the inner sides of the cover flap and the lower portion between the rear seam and the rear side and between the first and second sides;

wherein the pocket is configured to receive a splint therethrough.

2. The intravenous catheter securement device of claim 1 wherein the tabs comprise a first tab, a second tab and a third tab;

wherein the first tab is horizontally centrally disposed on the lower portion inner side with the lower securement portion disposed on an opposite of the slit from the upper securement portion;

wherein the second securement tab is vertically disposed between the opening and the first side in a position closer to the opening than the first side; and wherein the third securement tab is vertically centrally disposed between the opening and the second side.

3. The intravenous catheter securement device of claim 2 wherein the first, second, third and fourth attachment strips are formed of hook and loop fastener.

4. The intravenous catheter securement device of claim 3 wherein the inner side of each of the cover flap and the lower portion is a soft material;

wherein the inner side is configured to maintain warmth of the inner sides against a user's skin.

5. The intravenous catheter securement device of claim 4 wherein the soft material is polar fleece.

6. The intravenous catheter securement device of claim 5 wherein the middle layer of each of the cover flap and the lower portion is a thin foam rubber material.

7. The intravenous catheter securement device of claim 6 wherein the outer side of each of the cover flap and the lower portion is a water-resistant material.

8. The intravenous catheter securement device of claim 7 further comprising a logo is disposed on the cover flap exterior side.

9. An intravenous catheter securement device comprising: a protective dressing body configured to secure an intravenous catheter when in use, the dressing body comprising: a cover flap; a lower portion, each of the cover flap and the lower portion has a front side, a rear side, an inner side, an exterior side, a middle layer continuously disposed between the inner side and the exterior side, a first side, and a second side; wherein the inner side of each of the cover flap and the lower portion are continuously conjoined proximal to the rear side along a rear seam disposed between the first and second sides; a first attachment strip continuously disposed on the cover flap inner side proximal to the front side; a plurality of second attachment strips is continuously disposed on the cover flap exterior side proximal to the rear side between the first and second sides; a pocket continuously disposed between the inner sides of the cover flap and the lower portion between the rear seam and the rear side and between the first and second sides; wherein the pocket is configured to receive a splint therethrough; an opening centrally disposed on the lower portion between the front side and the rear side and between the first and second sides; a vertical slit is centrally continuously disposed on the lower portion between the front side and the opening; a plurality of spaced-apart tabs on the lower portion inner side proximal to the opening, each of the tabs comprising lower securement portion and an upper securement portion having a securement strip disposed proximal to an internal outer edge thereof removably attached to the lower securement portion; wherein the plurality of spaced-apart tabs comprise a first securement tab, a second securement tab and a third securement tab; wherein the first securement tab is horizontally centrally disposed on the lower portion inner side with the lower securement portion disposed on an opposite of the slit from the upper securement portion; wherein the second securement tab is vertically disposed between the opening and the first side in a position closer to the opening than the first side; and wherein the third securement tab is vertically centrally disposed between the opening and the second side; a third attachment strip is continuously disposed on the lower portion inner side between the first side and the second side in a central position between the front side and the first tab, wherein the first and third attachment strips removably engage each other; a fourth attachment strip is continuously disposed on the lower portion exterior side proximal to the front side, wherein the second and fourth attachment strips removably engage each other; wherein the first, second, third and fourth attachment strips are formed of hook and loop fastener; wherein the inner side of each of the cover flap and the lower portion is a soft material.

10. The intravenous catheter securement device of claim 9 wherein the soft material is polar fleece;

wherein the middle layer of each of the cover flap and the lower portion is a thin foam rubber material;

wherein the outer side of each of the cover flap and the lower portion is a water-resistant material.

11. The intravenous catheter securement device of claim 10 further comprising a logo is disposed on the cover flap exterior side.

* * * * *